United States Patent [19]

United States Patent [19]

Maffrand et al.

[11] 4,107,437
[45] Aug. 15, 1978

[54] 2,3-DIHYDROBENZOFURANS

[75] Inventors: Jean-Pierre Maffrand; Jean-Marie Pereillo, both of Toulouse, France

[73] Assignee: PARCOR, Paris, France

[21] Appl. No.: 792,504

[22] Filed: May 2, 1977

[30] Foreign Application Priority Data

May 31, 1976 [FR] France .................. 76 16370

[51] Int. Cl.² .......................................... C07D 405/12
[52] U.S. Cl. ................................. 544/376; 260/293.58;
  260/326.5 CA; 260/346.73; 424/248.57;
  424/250; 424/267; 424/274; 424/285; 544/153
[58] Field of Search ............... 260/268 BC, 346.2 R,
  260/293.58, 326.5 CA; 424/285; 544/153

[56] References Cited
U.S. PATENT DOCUMENTS

| 3,371,100 | 2/1968 | Howe ........................ 260/346.2 R |
| 3,457,281 | 7/1969 | Green et al. ................ 260/346.2 R |
| 3,470,185 | 9/1969 | Huebner et al. ............ 260/346.2 R |

Primary Examiner—Paul M. Coughlan, Jr.
Attorney, Agent, or Firm—Cushman, Darby & Cushman

[57] ABSTRACT 2,3-Dihydrobenzofuran of formula:

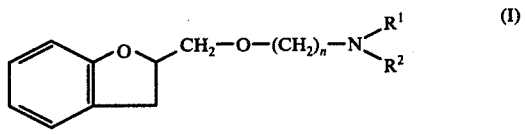

wherein $R^1$ and $R^2$ are each, independently, a lower alkyl or lower phenylalkyl or form, together with the nitrogen atom to which they are attached, a 4 to 8-membered saturated heterocyclic ring having 3 to 7 cyclic carbon atoms, a 4 to 8-membered saturated heterocyclic ring having 2 to 6 cyclic carbon atoms and two heteroatoms one of which is said nitrogen atom and the other is an oxygen atom, a sulphur atom or another nitrogen atom, said other nitrogen atom being optionally substituted by a phenyl, halophenyl, trifluromethylphenyl, lower alkylphenyl or lower alkoxyphenyl; $n$ is 2 or 3, and the salts thereof.

12 Claims, No Drawings

2,3-DIHYDROBENZOFURANS

The present invention relates to new 2,3-dihydrobenzofuran derivatives having the following formula:

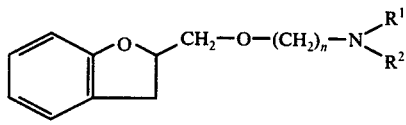

wherein $R^1$ and $R^2$ represent, independently of one another, an alkyl or aralkyl group or form, together with the nitrogen atom to which they are attached, a 4 to 8-membered saturated heterocyclic ring which may contain a second heteroatom such as oxygen, sulphur or nitrogen, which latter may be substituted by an organic group, particularly phenyl (which in turn may optionally carry a halogen, trifluoromethyl, lower alkyl or lower alkoxy substituent), and $n$ is 2 or 3; and the salts thereof.

The alkyl group and the alkyl portions of the aralkyl and alkoxy groups are advantageously straight-chained or branched lower ($C_1$ to $C_{12}$), preferably $C_1$ to $C_6$, groups. The aryl portion of the aralkyl may in particular be phenyl. The piperazino, morpholino, piperidino and pyrrolidino derivatives are particularly preferred.

The invention also includes the pharmaceutically acceptable inorganic or organic acid addition salts and quaternary ammonium derivatives of the compounds mentioned above.

The invention also provides a process for preparing the compounds of formula (I), characterized in that the benzo(b)furan derivative of formula (II) (S. W. Tinsley, J. Org., Chem., 1959, 24, 1197) is reacted with a haloalkylamine of formula III wherein $R^1$, $R^2$ and $n$ have the same meanings as above and X is a halogen, preferably chlorine, to obtain the compounds of formula I.

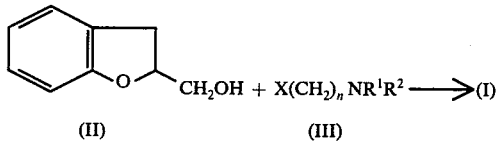

This reaction may, for example, be carried out in the presence of a 10–60% preferably 50% by weight, concentrated aqueous alkali metal hydroxide solution, particularly sodium hydroxide.

The reagents II and III are preferably used in stoichiometric quantities, but it is also possible to use one of the two reagents in excess. The temperature of the reaction medium is preferably maintained at between 50° and 100° C.

This preparative process uses an original reaction in a heterogeneous medium with a phase transfer catalyst. Catalysis is provided by the quaternary ammonium salts A and B obtained from dimerization and intramolecular cyclization, respectively, of the haloalkylamines of formula III.

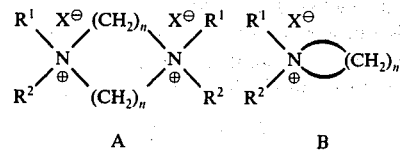

These haloalkylamines (III) are commercially available or may be prepared according to the processes described in Douglas C. Kriesel and Ole Gisvold, J. Pharm. Sci., 1967, 56 (3), 327 and J. Bourdais, Bull. Soc. Chim. Fr., 1968, (8), 3246.

The following non-restrictive examples are given to illustrate the preparation of the compounds according to the invention.

EXAMPLE 1

Preparation of 2-[(β-morpholinoethoxy)-methyl]-2,3-dihydrobenzo(b)furan (derivative no. 1); $NR^1R^2$ = morpholino, $n = 2$ A mixture of 9.4 g of N-(2-chloroethyl)-morpholine hydrochloride and 5 g of 2-hydroxymethyl-2,3-dihydrobenzo(b)-furan in 50 cc of 50% sodium hydroxide solution is heated to 120° C for 2 hours, with vigorous stirring. The mixture is diluted with water and extracted with ether. The ethereal extracts are washed with 6N hydrochloric acid. The aqueous acid phase is made basic with 2N sodium hydroxide solution and extracted with ether. These latter ethereal extracts are washed with water, dried over sodium sulphate and evaporated in vacuo.

The oil obtained is converted into the hydrochloride and, when recrystallized from a mixture of ethanol and diisopropyl ether, yields 7.6 g of white crystals (yield 76%), with a m.p. of 121° C, determined by the Kofler block method.

EXAMPLE 2

Preparation of 2-[(β-dimethylaminoethoxy)methyl]-2,3-dihydrobenzo(b)furan (derivative no. 2); $R^1 = R^2$ = methyl, $n = 2$ A mixture of 7.2 g of N,N-(2-chloroethyl)-dimethylamine hydrochloride and 5 g of 2-hydroxymethyl-2,3-dihydrobenzo(b)furan in 50 cc of 50% sodium hydroxide solution is heated to 120° C for 3 hours.

The mixture is then diluted with water and extracted with ether. The ethereal extracts are washed with water, dried over sodium sulphate and evaporated in vacuo. 6.6 g of oily product are obtained, which is converted into the hydrochloride. Recrystallization from a mixture of ethyl acetate and ethanol yields 4.1 g of white crystals (yield: 48%), m.p. 129° C determined by the Kofler block method.

EXAMPLE 3

Preparation of 2-[{2-(4-phenylpiperazino)-ethoxy}methyl]-2,3-dihydrobenzo(b)furan (derivative no. 3); $NR^1R^2$ = 4phenylpiperazino, $n = 2$ A mixture of 8.5 g of 1-(2-chloroethyl)-4-phenylpiperazine hydrochloride and 5.7 g of 2-hydroxymethyl-2,3-dihydrobenzo(b)furan in 70 cc of 50% sodium hydroxide solution is heated to 120° C for 2 hours. The reaction mixture is then diluted with water and extracted with chloroform. The chloroform extracts are washed with water, dried over sodium sulphate and filtered on a bed of silica. After evaporating off the solvent in vacuo, 12.2 g of oily product are obtained which is converted into the hydrochloride. 13.1 g of white crystals are obtained (yield: 84%), m.p. 130° C determined by the Kofler block method.

EXAMPLE 4

Preparation of 2-{[(3-(4-p-chlorophenylpiperazino)propoxy]methyl}-2,3-dihydrobenzo(b)furan (derivative no. 4); $NR^1R^2$ = 4-p-chlorophenylpiperazino, $n = 3$ A mixture of 7.7 g of 1-p-chlorophenyl-4-(3-chloropropyl)-piperazine hydrochloride and 3.8 g of 2-hydroxymethyl-2,3-dihydrobenzo(b)furan in 60 cc of 50% sodium hydroxide solution is heated to 120° C for 2 hrs. 30 minutes.

The mixture is diluted with water and extracted with ether. The ethereal extracts are washed with water, dried over sodium sulphate and concentrated in vacuo. 7.5 g of an oily product are obtained, which is converted into the oxalate. Recrystallization from ethanol yields 7.4 g of white crystals (yield: 62%), m.p. 157° C determined by the Kofler block method.

EXAMPLE 5

2-{[2-(4-p-chlorophenylpiperazino)-ethoxy]methyl}-2,3-dihydrobenzo(b)furan; $NR^1R^2$ = 4-p-chlorophenylpiperazino, $n = 2$.

dihydrochloride - white crystals - m.p. 130° C (ethanol); prepared using the method described in Example 1, yield 69%.

EXAMPLE 6

2-[(β-diethylaminoethoxy)methyl]-2,3-dihydrobenzo(b)furan; $R^1 = R^2$ = ethyl, $n = 2$.

oxalate, hemihydrate - white crystals - m.p. 105° C (ethyl acetate/ethanol); prepared using the method described in Example 1, yield 77%.

EXAMPLE 7

2-{[2-(4-m-chlorophenylpiperazino)ethoxy]methyl}-2,3-dihydrobenzo(b)furan; $NR^1R^2$ = 4-m-chlorophenylpiperazino, $n = 2$.

dihydrochloride - white crystals - m.p. 120° C (ethanol); prepared using the method of Example 2, yield 68%.

EXAMPLE 8

2-{[2-pyrrolidinoethoxy]-methyl}-2,3-dihydrobenzo(b)furan, $NR^1R^2$ = pyrrolidino, $n = 2$.

oxalate, white crystals, m.p. 97° C (ethanol/ethyl acetate); prepared using the method of Example 1, yield 48%.

EXAMPLE 9

2-[(β-piperidinoethoxy)methyl]-2,3-dihydrobenzo(b)furan, $NR^1R^2$ = piperidino, $n = 2$.

oxalate, white crystals, m.p. 116° C (ethanol); prepared using the method of Example 3, yield 82%.

EXAMPLE 10

2-{[2-(4-o-chlorophenylpiperazino)ethoxy]-methyl}-2,3-dihydrobenzo(b)furan; $NR^1R^2$ = 4-o-chlorophenylpiperazino, $n = 2$.

hydrochloride, white crystals, m.p. 126° C (ethyl acetate); prepared using the method of Example 3, yield 22%.

EXAMPLE 11

2-{[2-(4-m-trifluoromethylphenylpiperazino)-ethoxy]-methyl}-2,3-dihydrobenzo(b)furan, $NR^1R^2$ = 4-m-trifluoromethyl-piperazino, $n = 2$.

hydrochloride, white crystals, m.p. 165° C (ethanol/ethyl acetate); prepared using the method of Example 3, yield 37%.

EXAMPLE 12

2-{[2-(4-o-methoxyphenylpiperazino)ethoxy]-methyl}-2,3-dihydrobenzo(b)furan, $NR^1R^2$ = 4-o-methoxyphenyl-piperazino, $n = 2$.

dihydrochloride, white crystals, m.p. 175° C (isopropanol); prepared using the method of Example 3, yield 27%.

EXAMPLE 13

2-{[2-(4-p-tolylpiperazino)-ethoxy]-methyl}-2,3-dihydrobenzo(b)furan, $NR^1R^2$ = 4-p-tolylpiperazino, $n = 2$.

dihydrochloride, white crystals, m.p. 138° C (ethanol/ethyl ether); prepared using the method of Example 3, yield 65%.

EXAMPLE 14

2-[(3-dimethylamino-propoxy)-methyl]-2,3-dihydrobenzo(b)furan, $R^1 = R^2$ = methyl, $n = 3$.

oxalate, white crystals, m.p. 109° C (ethanol/ethyl ether); prepared using the method of Example 4; yield 64%.

EXAMPLE 15

2-{[3-(4-p-tolylpiperazino)-propoxy]methyl}-2,3-dihydrobenzo(b)furan, $NR^1R^2$ = 4-p-tolylpiperazino, $n = 3$.

dihydrochloride, white crystals, m.p. 156° C (ethanol/ethyl ether); prepared using the method of Example 4, yield 76%.

The results of the toxicological and pharmacological tests reported hereinafter demonstrate the good tolerance and interesting sedative and antiarrhythmic activities of the derivatives of the invention.

Thus, the invention also relates to a medicament having, in particular, sedative and antiarrhythmic activities, characterized in that it contains as active principle a derivative of formula I or a pharmaceutically acceptable acid addition salt or quaternary ammonium salt thereof.

I Toxicological study

This study showed the low toxicity and good tolerance of the derivatives of the invention.

As a guide, the $LD_{50}$/24 hours/kg of body weight, determined by the Miller and Tainter method, by intravenous route is, in mice, 72 mg for derivative No. 1, 52 mg for derivative No. 2, 45 mg for derivative No. 4, 40 mg for derivative No. 6, 54 mg for derivative No. 7, 29 mg for derivative No. 8, 28 mg for derivative No. 9, 33 mg for derivative No. 10, 70 mg for derivative No. 11 and 49 mg for derivative No. 14.

II Pharmacological study

This study dealt with sedative and antiarrhythmic activities.

1. Sedative activity a. Behavioral study

This study was carried out using the method of Samuel Irwin (Ph. D. Animal and Clinical Pharmacology Technics in Drug evaluation).

The derivatives of the invention are administered, by oesophageal tube, in a single dose of 100 mg/kg, to mice and rats which have been made to fast for 16 hours. A study of their behavior and different physiological parameters (temperature, cardiac and respiratory rate) shows the clear sedative and myorelaxant activity of these derivatives: in fact, starting at the 5th minute, a clear reduction in spontaneous motor activity, a slight reduction in responses to touch, a lowering in muscle tone and alertness, respiratory depression and reduced reactivity to noise and the environment were observed in all the animals.

b. Activity with regard to hypnotics

The compounds of the invention are administered by the oral route to different groups of mice in a dose of 100 mg/kg, 30 minutes before an intraperitoneal injection of a subhypnotic dose of sodium pentobarbital. The number of animals which fall asleep, the time taken to fall asleep and the length of sleep produced are noted. The results, summarized in Table I below, clearly demonstrate the significant potentiating activity of the compounds described, compared with the untreated control animals.

TABLE 1

| Treatment | Percentage of animals which fell asleep | Average time taken to fall asleep | Average length of sleep |
|---|---|---|---|
| 0 (control animals) | 0 | 0 | 0 |
| Derivative 1 | 80 | 8 min 30 s | 1 hr 45 min |
| Derivative 2 | 60 | 8 min 55 s | 1 hr 43 min |
| Derivative 3 | 70 | 9 min 15 s | 1 hr 35 min |
| Derivative 4 | 90 | 8 min 25 s | 1 hr 36 min |
| Derivative 5 | 80 | 8 min 48 s | 1 hr 58 min |
| Derivative 6 | 80 | 9 min 08 s | 1 hr 52 min |
| Derivative 7 | 70 | 9 min 00 s | 2 hr 10 min |
| Derivative 8 | 60 | 8 min 25 s | 1 hr 48 min |
| Derivative 9 | 70 | 8 min 40 s | 1 hr 55 min |
| Derivative 10 | 60 | 9 min 10 s | 1 hr 48 min |
| Derivative 11 | 100 | 8 min 25 s | 1 hr 39 min |
| Derivative 12 | 80 | 8 min 53 s | 2 hr 05 min |
| Derivative 13 | 90 | 8 min 20 s | 1 hr 54 min |
| Derivative 14 | 80 | 9 min 45 s | 1 hr 48 min |
| Derivative 15 | 90 | 8 min 28 s | 1 hr 50 min | c. The 4 plate test (Boissier, Simon & Aron, Europ J. Of. Pharmacol 4, 1968, 145 to 151)

A mouse placed in an enclosure containing 4 electrified plates receives an electric shock causing random flight each time it moves from one plate to another.

After n electric shocks, the mouse has stopped moving. The degree of tranquillization obtained is considered to be proportional to the number n of electric shocks which the treated mouse has received before staying motionless in a corner. Thus, administered by the oral route, in a dose of 100 mg/kg the derivatives of the invention produce a substantial percentage increase in the number of electric shocks n after 15, 45 and 90 minutes.

The results are summarized in Table II below:

TABLE II

| | Average increase in n | | |
|---|---|---|---|
| Treatment | After 15 minutes | After 45 minutes | After 90 minutes |
| Derivative 1 | 64 | 62 | 33 |
| Derivative 2 | 62 | 62 | 30 |
| Derivative 3 | 59 | 60 | 29 |
| Derivative 4 | 65 | 64 | 32 |
| Derivative 5 | 57 | 64 | 34 |
| Derivative 6 | 59 | 62 | 31 |
| Derivative 7 | 58 | 59 | 28 |
| Derivative 8 | 61 | 60 | 35 |
| Derivative 9 | 58 | 59 | 29 |
| Derivative 10 | 62 | 62 | 31 |
| Derivative 11 | 60 | 61 | 28 |
| Derivative 12 | 65 | 62 | 27 |
| Derivative 13 | 59 | 59 | 30 |
| Derivative 14 | 61 | 61 | 32 |
| Derivative 15 | 59 | 62 | 33 |

2. Antiarrhythmic activity

The tests were carried out on rabbits and dogs using the method of H. Schmitt and H. Schmitt (Arch. Int. Pharmacodyn. 1960, 127 (12)) : barium chloride injected intraveneously in an average dose of 3 mg/ml kg causes the immediate appearance of polymorphic ventricular extrasystoles which last for about 15 minutes. Tests showed that the derivatives of the invention administered orally in a dose of 30 mg/kg protected the test animals from the induced arrhythmia, in a proportion of from 95 to 100%; in fact, bursts of extrasystoles, or regular or dispersed extrasystoles did not occur in the treated animal.

This same property of the derivatives of the invention is also found with regard to other arrhythmia-inducing agents such as aconitine, calcium chloride, K-strophantine, isoprenalin, adrenalin and ouabain.

The antiarrhythmic properties of the compounds of formula I were also studied using the method of experimental ventricular arrhythmia (Harris A.S., circulation 1950, 1, (6) 1218). Tying off the anterior intraventricular coronary artery for a time produces anoxaemia which causes electrophysiological changes in the myocardiac cells. This results in ventricular tachycardia or polymorphic arrhythmia which sets in 4 hours after the artery is tied off and reaches a maximum intensity 10 to 20 hours after the operation, disappearing again after 72 hours. It was found that the administration of the derivatives of the invention by the parenteral route, at the moment when the disorders have reached the maximum intensity, rapidly re-establishes the sinusal rhythm and improves the disturbed electrical activity of the heart, whilst restoring rhythmic ventricular activity.

The toxicological and pharmacological studies described above demonstrated the important sedative and antiarrhythmic activity of the derivatives of formula I.

The medicaments of the invention may be formulated as coated tablets, capsules, drops or syrups, for oral administration. For rectal administration they may also take the form of suppositories and, for parenteral administration, they may be in the form of injectable solutions.

Each dosage unit of from 0.1 to 5 g advantageously contains from 0.025 g to 0.250 g of active principle, whilst the doses to be administered daily may vary from 0.025 g to 1 g of active principle.

Some pharmaceutical formulations of the medicaments of the invention will be given hereinafter as non-restrictive examples.

1. Coated tablets
   core    Derivative No. 2    0.050 grams
           lactose, magnesium stearate, kaolin, starch
   coating  Eudragit S, shellac, gum arabic, carnauba wax,
           starch, gelatine, saccharose, tartrazine yellow.
2. Tablets
           Derivative No. 6    0.080 grams
   excipient: starch, kaolin, magnesium stearate, erythrosine.
3. Capsules
           Derivative No. 3    0.100 grams
   excipient: talc, lactose, magnesium stearate -continued

| 4. Syrup | |
|---|---|
| Derivative No. 7 | 0.600 grams |
| sweetened flavored excipient q.s. ad 100 ml | |
| 5. Suppositories | |
| Derivative No. 10 | 0.075 grams |
| excipient: semi-synthetic triglycerides | |
| 6. Injectable Solution | |
| Derivative No. 14 | 0.050 grams |
| isotonic solution q.s. ad 5 ml | |

On account of their important sedative and antiarrhythmic properties, the medicaments of the invention can be used to advantage in human and veterinary medicine.

They may be administered as a sedative for reducing anxiety and behavioral disorders and for normalizing sleep without effecting alertness and intellectual functions. They are indicated in anxiety states, sleep disorders, behavioral disorders, irritability and instability.

By virtue of their antiarrhythmic activity, they are indicated in the treatment of disorders of cardiac rhythm (auricular fibrillation and flutter, auricular, ventricular or polymorphic extrasystoles, tachycardia) and in the prevention of disorders of cardiac rhythm following anterior infarction.

What we claim is:

1. 2,3-dihydrobenzo(b)furan of the formula

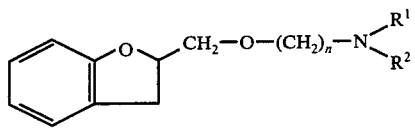

wherein
R$^1$ and R$^2$ each independently represent alkyl having 1–12 carbon atoms, phenyl alkyl wherein the alkyl moiety has 1–12 carbon atoms or together with the nitrogen atom to which they are attached form morpholino, phenylpiperazino, halophenylpiperazino, pyrrolidino, piperidino, trifluoromethylphenylpiperazino, alkyl phenyl piperazino, having up to 12 carbon atoms in the alkyl moiety or alkoxyphenylpiperazino having up to 12 carbon atoms in the alkoxy moiety;
n is 2 or 3; and the pharmaceutically acceptable salts thereof.

2. 2,3-dihydrobenzo(b) furan of the formula

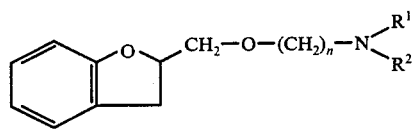

wherein
R$^1$ and R$^2$ each independently represent alkyl having 1–12 carbon atoms or together with the nitrogen atom to which they are attached form morpholino, phenylpiperazino, halophenylpiperazino, pyrrolidino, piperidino, trifluoromethylphenylpiperazino, alkyl phenyl piperazino wherein the alkyl moiety has 1–12 carbon atoms or alkoxyphenylpiperazino wherein the alkoxy moiety has 1–12 carbon atoms and
n is 2 or 3; and
the pharmaceutically acceptable salts thereof.

3. 2,3-dihydrobenzo(b) furan of the formula

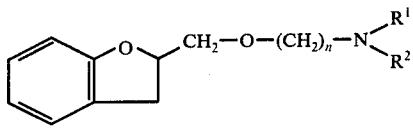

wherein
R$^1$ and R$^2$ each independently represent methyl or ethyl, or together with the nitrogen atom to which they are attached form morpholino, phenylpiperazino, chlorophenylpiperazino, pyrrolidino, piperidino, trifluoromethylphenylpiperazino, methylphenylpiperazino or methoxyphenylpiperazino; and
n is 2 or 3; and
the pharmaceutically acceptable salts thereof.

4. The 2,3-dihydrobenzo(b) furan of claim 1 wherein

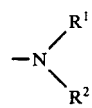

is piperazino.

5. The 2,3-dihyrobenzo(b) furan of claim 1 wherein

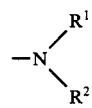

is piperazino substituted by phenyl, halophenyl, trifluoromethylphenyl, alkylphenyl wherein the alkyl moiety has 1–12 carbon atoms or alkoxyphenyl wherein the alkoxy moiety has 1–12 carbon atoms.

6. The 2,3-dihydrobenzo(b) furan of claim 1 which is 2-[[2-(4-phenylpiperazino)-ethoxy]methyl]-2,3-dihydrobenzo(b) furan or pharmaceutically acceptable salts thereof.

7. The 2,3-dihydrobenzo(b) furan of claim 1 which is 2-[[3-(4-p-chlorophenylpiperazino)-propoxy]methyl]-2,3-dihydrobenzo(b) furan or pharmaceutically acceptable salts thereof.

8. The 2,3-dihydrobenzo(b) furan of claim 1 which is 2-[[2-(4-p-chlorophenylpiperazino)-ethoxy]methyl]-2,3-dihydrobenzo(b) furan or pharmaceutically acceptable salts thereof.

9. The 2,3-dihydrobenzo(b) furan of claim 1 which is 2-[[2-(4-m-chlorophenylpiperazino)-ethoxy]methyl]-2,3-dihydrobenzo(b) furan or pharmaceutically acceptable salts thereof.

10. The 2,3-dihydrobenzo(b) furan of claim 1 which is 2-[[2-(4-o-chlorophenylpiperazino)-ethoxy]methyl]-2,3-dihydrobenzo(b) furan or pharmaceutically acceptable salts thereof.

11. The 2,3-dihydrobenzo(b) furan of claim 1 which is 2-[[2-(4-p-tolylpiperazino)-ethoxy]methyl]-2,3-dihydrobenzo(b) furan or pharmaceutically acceptable salts thereof.

12. The 2,3-dihydrobenzo(b) furan of claim 1 which is 2-[[3-(4-p-tolylpiperazino)-propoxy]methyl]-2,3-dihydrobenzo(b) furan or pharmaceutically acceptable salts thereof.

* * * * *